US004001657B2

United States Statutory Invention Registration [19]

[11] Reg. Number: H1657

Hammons et al.

[45] Published: Jun. 3, 1997

[54] ABSORBENT ARTICLE WITH FRACTIONATION MEMBER

[75] Inventors: John L. Hammons, Hamilton; James C. Horney, Cincinnati, both of Ohio

[73] Assignee: The Procter & Gamble Company, Cincinnati, Ohio

[21] Appl. No.: 382,921

[22] Filed: Feb. 3, 1995

[51] Int. Cl.[6] ..... A61F 13/52

[52] U.S. Cl. ..... 604/385.1; 604/378

[58] Field of Search ..... 604/378, 385.1, 604/385.2, 367, 368

[56] References Cited

U.S. PATENT DOCUMENTS

| | | | |
|---|---|---|---|
| 3,371,667 | 3/1968 | Morse | 604/369 |
| 3,663,348 | 5/1972 | Liloia et al. | 428/171 |
| 3,700,544 | 10/1972 | Matsui | 428/373 |
| 3,726,277 | 4/1973 | Hirschman | 604/359 |
| 4,047,531 | 9/1977 | Karami | 604/374 |
| 4,085,754 | 4/1978 | Ness et al. | 604/390 |
| 4,223,677 | 9/1980 | Anderson | 604/378 |
| 4,321,924 | 3/1982 | Ahr | 604/378 |
| 4,323,069 | 4/1982 | Ahr et al. | 604/378 |
| 4,324,246 | 4/1982 | Mullane et al. | 604/366 |
| 4,324,247 | 4/1982 | Aziz | 604/371 |
| 4,372,312 | 2/1983 | Fendler et al. | 604/370 |
| 4,578,071 | 3/1986 | Buell | 604/379 |
| 4,636,209 | 1/1987 | Lassen | 604/378 |
| 4,643,727 | 2/1987 | Rosenbaum | 604/369 |
| 4,723,953 | 2/1988 | Rosenbaum et al. | 604/369 |
| 4,798,603 | 1/1989 | Meyer et al. | 604/378 |
| 4,898,642 | 2/1990 | Moore et al. | 162/157.6 |
| 5,004,465 | 4/1991 | Ternström et al. | 604/385.1 |
| 5,009,650 | 4/1991 | Bernardin | 604/378 |
| 5,019,062 | 5/1991 | Ryan et al. | 604/359 |
| 5,057,368 | 10/1991 | Largman et al. | 428/397 |
| 5,135,521 | 8/1992 | Luceri et al. | 604/383 |
| 5,147,345 | 9/1992 | Young et al. | 604/378 |
| 5,217,445 | 6/1993 | Young et al. | 604/378 |
| 5,262,223 | 11/1993 | Palumbo et al. | 428/195 |
| 5,281,208 | 1/1994 | Thompson et al. | 604/378 |
| 5,300,054 | 4/1994 | Feist et al. | 604/378 |
| 5,334,176 | 8/1994 | Buenger et al. | 604/367 |
| 5,364,382 | 11/1994 | Latimer et al. | 604/378 |

FOREIGN PATENT DOCUMENTS

| | | |
|---|---|---|
| 483592A1 | 5/1992 | European Pat. Off. . |
| 2061115 | 10/1979 | United Kingdom . |
| 2061115 | 5/1981 | United Kingdom . |

*Primary Examiner*—Michael J. Carone
*Assistant Examiner*—Matthew J. Lattig
*Attorney, Agent, or Firm*—Phillip A. Rotman, II; William Scott Andes; E. Kelly Linman

[57] ABSTRACT

An absorbent article for the management of body exudates having in combination, an acquisition component and a storage component. The acquisition component, interposed between the source of body exudates and the fluid storage component, has a member for fractionating body exudates emanating from the source and for storing the solid portion of the body exudates. The acquisition component has a plurality of pores in the size range of red blood cells, suspended solids, and other body exudates which traps, and stores the solid portion of body exudates and allows the fluid portion to continue flowing through the acquisition component and into the storage component. The storage component is for storing the fluid portion of the body exudates.

20 Claims, 2 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ABSORBENT ARTICLE WITH FRACTIONATION MEMBER

TECHNICAL FIELD OF THE INVENTION

The present-on relates generally to an absorbent article for storing body exudates and more specifically to an absorbent structure that acquires and stores body exudates.

BACKGROUND OF THE INVENTION

Disposable absorbent articles for acquisition and storage of body exudates (e.g., urine, feces, blood, vaginal discharge, saliva, etc.) are well known in the prior art and have been provided for many uses in various configurations. Typical examples include disposable diapers or incontinence pads which are intended to absorb and retain urine and feces; wound dressings (e.g. bandages) which are intended to absorb and retain blood; and catamenial pads which are intended to absorb and retain menstrual and other vaginal discharges, and prevent body and clothing soiling. In each, the disposable absorbent article absorbs and retains body exudates, thereby preventing the exudates from soiling or otherwise contaminating the area (e.g. the clothes or the wearer) around the body exudates discharge.

In general, disposable absorbent articles have the same basic structure: an absorbent structure, which is encased between a topsheet, which is in contact with the wearer, and a backsheet. The prior art teaches numerous variations of these elements, with each variation being directed to improving one or more specific characteristics of the absorbent article.

A catamenial product (e.g. a sanitary napkin, a pantiliner or a tampon) is distinguishable from other types of absorbent articles in that its materials must absorb, distribute, store, and retain vaginal discharges (e.g. menstrual and other vaginal discharges), which are distinguishable from other types of discharged body exudates, such as urine, which is typically absorbed by a diaper. Urine is characterized as a Newtonian fluid and has a relatively constant viscosity. A vaginal discharge, on the other hand, is a complex and heterogeneous suspension that is characterized as a non-Newtonian fluid (e.g., a fluid that generally does not maintain a constant viscosity throughout and does not follow typical flow patterns because of the high solid content). As will be appreciated, menstrual discharges typically comprise a non-solid or fluid portion, having water, and a solid portion having various elements, such as body tissue fragments, protein aggregates, lipids etc., each of which contribute to the non-Newtonian fluid characteristic. The composition of menstrual discharge varies from woman to woman, and even from day to day with an individual woman.

There are numerous absorbent articles in the prior art with storage components that are interposed between a backsheet and an acquisition component. The acquisition component of these articles typically is a material configured so that it quickly absorbs and wicks exudates away from the wearer and topsheet, and toward and into the storage component. Such articles also are configured so that exudates do not flow back toward the wearer reducing the possibility of "rewetting". This provides comfort for the wearer of the article since the skin of the wearer remains relatively dry. The storage component is a material provided in absorbent articles to absorb exudates from the absorbent component, and that can store and redistribute the absorbed exudates.

Several materials have been developed, especially in the area of disposable diapers, which provide enhanced storage capacity and redistribution properties (e.g. wicking).

Examples of such materials include small pore polymeric foam materials, which have a storage capacity of about five (5) times the storage capacity of fiber materials, and about 30 to 50 times its own weight. Unfortunately, these polymeric foam materials have not previously been viable in catmenial products since some of the open spaces are similarly sized to red blood cells, and suspended solids, which are typically found in vaginal discharges. The solid portion of the vaginal discharge tends to block or clog the open spaces which, in turn, limits storage capacity and the redistribution capability therein.

Another material with enhanced storage capacity is a superabsorbing hydrogel material dispersed in fiber matrix which has storage capacity for artificial menstrual fluid from about 8 to about 16 times greater than its own weight, and from about 25 to about 30 times it own weight for urine. Also, the material has a storage capacity from about 2 to about 3 times greater than fiber materials. Like the polymeric foam materials discussed above, superabsorbing polymers dispersed in a fiber matrix were not as viable in catamenial products since the solid portion in vaginal discharge can plate the outer surface of superabsorber particles, which reduces their capacity to absorb and store the discharge. This problem is not unique to polymeric foam materials or superabsorbing hydrogel material in a sheet form or dispersed in fiber matrix, and can exist with any absorbent material having a high concentration of small pores or openings. Examples of such materials include other foams, superabsorbers, sheeted superabsorbers, dense fiber materials and the like.

It is an object of the present invention to provide an absorbent structure that allows the use of highly effective storage materials in absorbent structures.

It is also an object of the present invention to provide an absorbent structure with an extended useful life.

It is another object of the present invention to provide an absorbent structure with increased storage capacity.

It is still another object of the present invention to provide an absorbent structure having improved surface cleanliness to have a good visual appearance.

Another object of the present invention is to provide an absorbent structure having improved protection against soiling in the area around the area of exudate discharge.

Additional objects, advantages and other features of the present invention will be set forth and will become apparent to those skilled in the art upon examination of the following, or may be learned with practice of the invention.

SUMMARY OF THE INVENTION

To achieve the foregoing and other objects, and in accordance with the purpose herein, the present invention comprises an absorbent article for the management of body exudates having, in combination, a storage component and an acquisition component. The storage component is for storing the fluid portion of body exudates. The acquisition component, interposed between the source of body exudates and the storage component, is for filtering and storing the solid portion of the exudates. The acquisition component has a plurality of pores in the size range of red blood cells, suspended solids, and other body exudates which traps the solid portion of the body exudate and allows the fluid portion to continue flowing through the acquisition component and into the storage component.

In a preferred embodiment, the acquisition component can include curled cellulosic fibers being mechanically altered from an unrefined state to a refined state, and the storage component can include either a flexible hydrophilic polymeric foam material or a superabsorbing hydrogel material disposed in a fiber matrix.

In a presently preferred embodiment of the present invention, the absorbent article comprises a topsheet or can comprise a topsheet and a backsheet.

BRIEF DESCRIPTION OF THE DRAWINGS

While the specification concludes with claims particularly pointing out and distinctly claiming the present invention, it is believed that the same will be better understood from the following description taken in conjunction with the accompanying drawings, in which:

DETAILED DESCRIPTION OF THE PREFERRED EMBODIMENT

Figure 1:
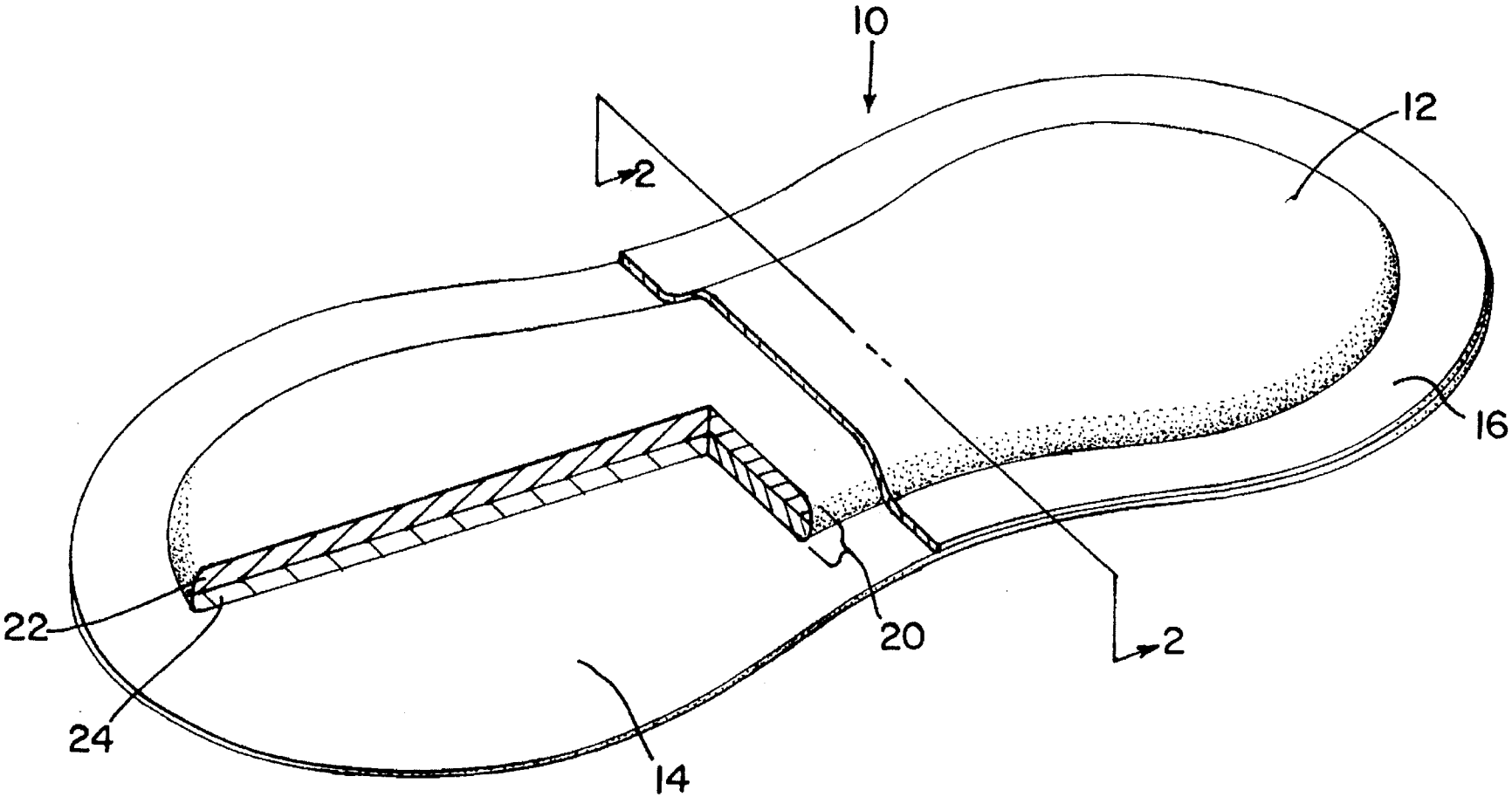
FIG. 1 is a cutaway elevated perspective view of an exemplary absorbent article made in accordance with the present invention.

Referring now to the drawing figures in detail, where like numerals indicate the like element throughout the views, there is shown a preferred embodiment of the present invention as it would be used in a disposable absorbent article, and in particular, in a catmenial pad.

As used herein, the term "absorbent article" refers to articles which absorb and contain body exudates. More specifically, the term refers to articles which are placed against or in close proximity to the body of the wearer to absorb and retain various exudates, including those discharged from the body. It should be understood, however, that the present invention is also applicable for use in other disposable "absorbent articles" such as pantiliners, diapers, incontinence pads, bandages, wound dressings, bed pads, tampons and the like.

As used herein, the term "disposable absorbent article" refers to articles which are intended to absorb and contain exudates, such as those discharged from the body (e.g., blood, vaginal discharges, urine, and the like), and further, which articles are intended to be discarded after a single use. (e.g., they are not intended to be laundered or otherwise restored and then reused). A catamenial pad (e.g., a sanitary napkin or pantiliner) is a disposable absorbent article worn by females external to the urogenital region and which is intended to absorb and contain menstrual fluids and other vaginal discharges.

As used herein, the term "solid portion of the body exudate" refers to particles having an effective radii of greater than about 5 μm.

Figure 2:
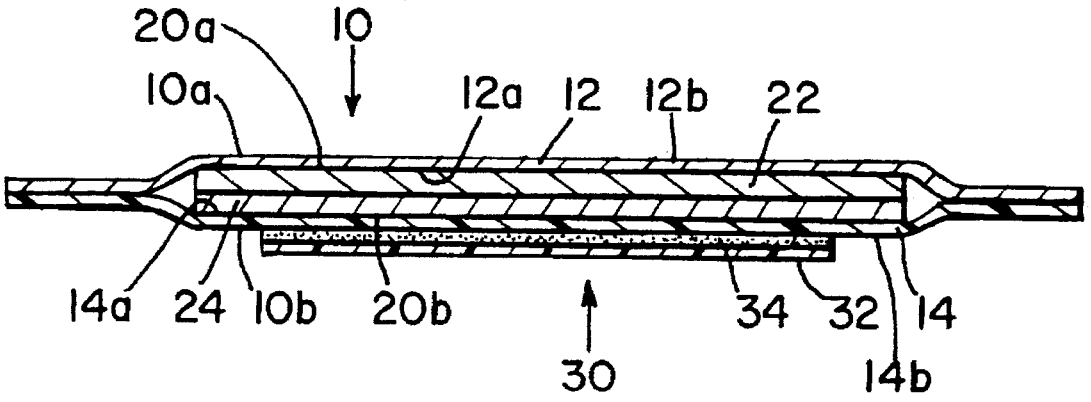
FIG. 2*a* is a cross sectional view of the absorbent article of FIG. 1 taken along line 2—2 thereof.

As best seen in FIG. 2, however, the absorbent article 10 has two surfaces, a body facing surface 10*a* and a garment facing surface 10*b*. The body facing surface 10*a* is intended to be worn adjacent to the body of the wearer whereas the garment facing surface 10*b* is on the opposite side of article 10 and is intended to be placed adjacent to the undergarment of the wearer when the article 10 is worn.

The sanitary napkin should not be bulky to wear and should be sized and configured to fit under clothing to be less noticeable. As such, napkins can be of any thinness, and would generally have a thinness (i.e., caliper) of less than about 10 mm, with some having a thinness of less than about 7 min. The surface area of the body facing surface 10*a* should be at least about 100 $cm^2$ to prevent discharged exudates from missing the absorbent article 10 and soiling clothing or the body of the wearer. The absorbent article 10 should also preferably be relatively flexible so that it readily conforms to the crotch area of the undergarment of the wearer and the anatomy of the wearer, and that it is comfortable to the wearer.

Basically, the absorbent article 10 can include a fluid permeable topsheet 12, a backsheet 14 (or "barrier means"), and an absorbent structure 20 which includes an acquisition component 22 in close proximity to the topsheet 12 and a storage component 24 interposed between the backsheet 14 and the acquisition component 22. The outer surface of backsheet 14 can double as the garment facing surface 10*b*, and can be in close proximity to the use's undergarment. The outer surface of topsheet 12 can double as the body facing surface 10*a*, and is placed in close proximity to the users body when the absorbent article 10 is used.

The topsheet 12 and backsheet 14 are preferably affixed to each other in any manner and any configuration as is known in the industry. Typical examples include using glue, crimping or heat seals which extend around the periphery of both topsheet 12 and backsheet 14.

In a preferred manner and configuration of affixing the topsheet 12 and backsheet 14 together, both are manufactured having a shape similar to, but generally larger than, the absorbent structure 20, as seen best in FIG. 1. Thus, the topsheet 12 and backsheet 14 generally have a portion extending outward from the edges (e.g., the lateral and longitudinal edges) of the absorbent structure 20, thereby forming a narrow and flexible border 16 which encircles the absorbent structure 20.

The configuration of the structure 20 should cover the greatest possible area in the crotch portion of a wearer's undergarment, and suitable examples of the shape of the absorbent article 10 include a rectangular shape, a dog-bone shape, an hourglass shape, a sinusoidal shape, or an elongated pear shape.

The absorbent article 10 of the present invention can also be provided with any optional additional components that are known in the art, and may include side panels, an adhesive fastening element or a removable cover strip or release liner. The absorbent article 10 may be provided with flexible side panels 40, that can be folded around the crotch portion of the wearers panties, as disclosed in U.S. Pat. No. 4,589,876, to Van Tilburg, the disclosure of which is hereby incorporated herein by reference. The fastening component 30 serves to attach the absorbent article 10 to the undergarment of the wearer, and the removable release liner 32 covers the adhesive element 34 in order to keep the adhesive dement 34 from drying out or sticking to a surface other than the crotch portion of the undergarment prior to use. Typically, a fastening component 30 comprises an adhesive element 34 provided on the outer surface of backsheet 14 and a release liner 32. To apply the napkin to an undergarment, release liner 32 for the adhesive element 34 is removed and the adhesive element 34 secures the absorbent article 10 directly to the undergarment of the wearer. Generally, absorbent article 10, such as catamenial pads, are placed in the crotch portion of an undergarment. Other fastening components can be used, including belts, clips and other devices known in the art.

Each of the elements of the present invention will now be explained in greater detail.

Figure 3:
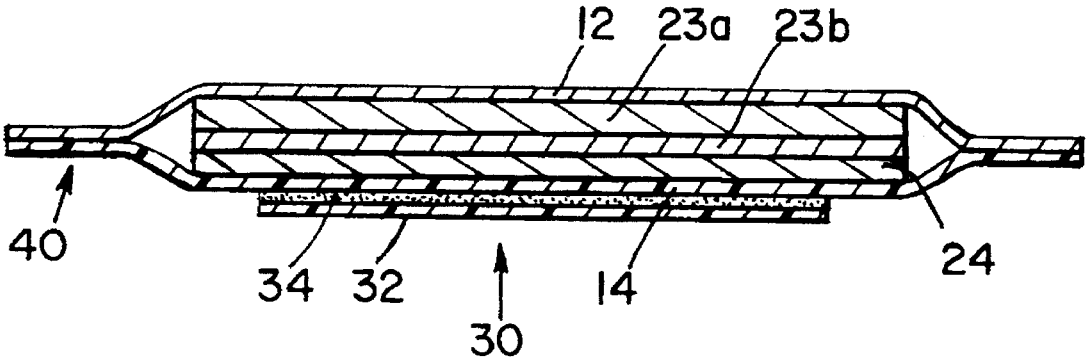
FIG. 3 is a cross sectional view of an alternative embodiment of the present invention formed with flexible side panels.

FIGS. 1 through 3 illustrate a topsheet 12 that overlies and is folded around other components of article 10, and also has a structure-facing side 12*a* and a bodyfacing side 12*b*, which also generally form a portion of the body surface 10*a* of the absorbent article 10. In use, body-facing side 12*b* of topsheet 12 is placed closest or next to the skin of the wearer adjacent to the body orifice (e.g., urogenital region) to receive body exudates. Topsheet 12 should be pervious to exudates and comprise relatively hydrophobic materials in comparison with the other materials of the absorbent structure 20 so that exudates are permitted to rapidly penetrate and transfer therethrough toward the structure 20. The material will preferably have no affinity for retaining body exudates in the area of contact between topsheet 12 and the skin of the wearer. In addition to exhibiting good strike through characteristics, the material should also reduce the tendency of the absorbent article 10 to "re-wet" (e.g., allowing the exudates to flow back through the topsheet 12 to the wearer's skin) and should be flexible material (e.g., readily conforms to the body shape, compliant, or respond by easily deforming in the presence of external forces) that is non-irritating to the wearer's skin. For aesthetic purpose, topsheet 12 should be clean in appearance and somewhat opaque to hide exudates stored in structure 20.

The topsheet 12 preferably also has a plurality of apertures to permit exudates deposited thereon to pass through to the structure 20. Such apertures may, but need not, also be present in any extension of the topsheet 12 may comprise a portion of the side panels 40. If apertured, the topsheet 12 should have from about 5% to about 60% open area, preferably about 25%, and should have a thinness from about 0.01 mm to about 0.05 min.

Suitable topsheets 12 can be made in part or completely of a number of different materials, such as, non-woven materials or perforated film comprising such materials as polyester, polyethylene, polypropylene, polyolefin, rayon, or the like, or of natural fibers such as cottons, foams, or combinations thereof using any suitable process. In non-woven topsheet materials, the fibers are typically bound together by a thermal binding process, or by a polymeric binder, such as polyacrolate, which is substantially porous and permits exudates to readily pass therethrough into the underlying absorbent structure 20.

If desired, a suffactant can also be added to the material used in topsheet 12 to render it more hydrophilic which enhances exudate penetration therethrough. In turn, the use of a surfactant reduces the exudate off flow (e.g., side soiling or end soiling) from the topsheet 12. A suitable surfactant should be nonionic, should not irritate the skin of the wearer, and should be evenly spaced and completely distributed through the material at a distribution of about 0.01 mg of suffactant per square centimeter of topsheet 12. A suitable illustrative example of a suffactant usable with the present invention is sold by Glyco Chemical, Inc. of Greenwich, Conn., as Pegosperse 200.

Suitable illustrative examples of preferable topsheets 12 include topsheets made in accordance with the teachings of U.S. Pat. Nos. 4,342,314, to Radel et al., and 4,463,045, to Ahr, et al. the disclosure of both patents which is hereby incorporated herein by reference.

As stated previously, absorbent article 10 further comprises a backsheet 14 that assists in preventing the exudates from soiling articles which come into contact with the wearer, such as the panty or clothing of the wearer. As shown in FIG. 2, the backsheet 14 is superimposed and co-extensive on its core facing side 14*a* with at least a portion of the backing facing side 20*b* of structure 20. Additionally, backsheet 14 also has a garment-facing side 14*b* which is typically adjacent the garment of the wearer, and forms a portion of the garment side 10*b* of absorbent article 10. The structure-facing side 14*a* can be distinguished from the garmentfacing side 14*b* of backsheet 14 because the structure-facing side 14*a* is joined to the topsheet 12 and structure 20. The backsheet 14 can be constructed from a thin, plastic film of flexible material which is substantially water impervious, and prevents collected discharged exudates from moving through and escaping from the absorbent article 10, and soiling the body or clothing of the wearer. Such materials may also be impervious to malodorous gases generated by body discharges, which, in turn, reduce the opportunity for discharge gases to escape and become noticeable to the wearer or others.

As discussed previously, absorbent article 10 further comprises an absorbent structure 20 that absorbs and redistributes exudates for storage while maintaining comfort and non-irritation for the wearer's skin, and further prevents soiling of the wearer's undergarment, outer clothing, or skin. To function as an effective catamenial pad, the absorbent structure 20 should generally have a thin and narrow configuration, especially in the crotch area, so as to be comfortable, as discussed above, and should have an absorbent capacity depending on the intended use of the absorbent article while still remaining comfortable. The structure 20 should be sized to register with the topsheet 12 and backsheet 14, and may be configured of any suitable shape, and preferably can be a rectangular shape, an elongated pear-shaped, a sinusoidal shape, a dog-bone shape, or an hour-glass shape, as shown in FIG. 1.

So long as the acquisition component 22 and storage component 24 are in fluid communication with each other, they may be interposed relative to one another in a wide variety of configurations. In any structure, it is desirable to employ minimal amounts of the components of the absorbent structure 20 (e.g., the materials of the acquisition component 22 and the storage component 24) while providing adequate absorption, distribution, and storage of exudates with minimal leakage of the exudates. The selection of materials and interaction of the particular configuration of the acquisition and storage components 22 and 24, respectively, utilized in absorbent structure 20 result in an especially efficient handling of exudates and, in turn, permits utilization of minimal amounts of materials in each of their respective components (e.g., 22 and 24).

The acquisition component 22 is preferably positioned in close proximity to topsheet 12 and interposed between topsheet 12 and storage component 24. Since the discharge of the body exudates (i.e., vaginal discharge) occur in a particular area, the acquisition component 22 should preferably encompass the urovaginal region for catamenial pads, so as to be effectively located to acquire and transport body exudates to other regions of the absorbent structure 20.

In accordance with the teachings of the present invention, the acquisition component 22 has larger pore sizes relative to the pore sizes of the storage component 24 such that the acquisition component 22 can acquire body exudates and can also filter and retain (e.g., store) the solid portion of the exudates while transporting (e.g., wicking or partitioning) the remaining fluid portion of body exudates to the storage component 24 for redistribution and storage. For components 22 and 24 to function as such, the acquisition component 22 should have a higher percentage of pore sizes larger than the range of pore sizes the storage component 24.

The acquisition component 22 will preferably comprise a material that fractionates or filters the solid portion from the fluid portion of the body exudates. More specifically, particles in menstrual discharges and other vaginal discharges having an effective radii of greater than about 5 μm are removed by fractionation or filtering and stored in the acquisition component 22. Optimally, this allows the fluid portion of the body exudates to be stored in the storage component 24. The materials for use as acquisition component 22 should fractionate or filter the menstrual discharge as it moves or redistributes therethrough, and retains or stores the fractionated component therein. Large debris in the menstrual discharge, can become trapped or lodged in the larger capillaries (e.g., 45 to 150 μm radii) of the acquisition component 22. As the resistance to the flow of exudates increases, the smaller capillaries (e.g., 5 to 45 μm radii) are required to "pull" the body exudates toward the storage component 24, and these smaller capillaries trap and retain the smaller particles and debris in the exudates, and thereby "fractionate" which results in that portion being stored therein. As the body exudates move through the smaller pores, near complete separation of fluid and solid portions occurs, and "visual" fractionation results whereby the exudates change color appearances.

As exudates move through the acquisition component 22, a certain amount of the exudate should move in a horizontal direction outwardly from the initial area of contact with the acquisition component 22, which is typically in the crotch region of the article 10. The wicking of the exudates further enhances fractionation of exudates, as discussed above, which in turn further enhances the fluid portion of exudates partitioning to the material of the storage component 24.

If solid portions of exudates, such as debris and particles, are transported to the storage component 24, reduction of the storage capacity of the storage component 24 can result, which, in turn, can lead to premature failure (e.g., soiling of the body or garments of the wearer) of the article (e.g., 10). Specifically, the particles and debris of exudates can block, clog, cover, coat, or plate the small surface pores of the storage component 24. The present invention provides an absorbent structure 20 which has an extended usage time by providing a more complete utilization of the absorbent structure 20 due to fractionation and storage of the solid portion of exudates in the acquisition component, which enhances exudate distribution in the fine capillary structure of the storage component 24.

Suitable examples of materials that will acquire and trap (e.g., store) non-fluid portions of the body exudates include refined, wet laid, chemically cross-link and stiffened, twisted fibers. As discussed more fully in U.S. Pat. No. 4,898,642 to Moore, et al., the disclosure of which is hereby incorporated herein by reference, cuffed fibers can have an average dry fiber twist count of at least about 4.5 twist nodes per milliliters, an average wet fiber twist count of at least about 3.0 twist nodes per milliliters, and at least about 0.5 twist nodes per milliliters less than the fiber twist count. Furthermore, the average isopropyl alcohol retention value is less than about 30%, and, the average water retention value is between about 28% and about 50%. Preferred fibers have an average dry fiber curl factor of at least about 0.30, and more preferably at least about 0.50. It is to be understood that the refining process does not substantially affect these parameters because the process is carried out in a manner where there is little or no defibrillation of the original curled and twisted fibers. Rather, the original fibers are, in general, reduced in length, and on the average, have original lengths ranging approximately from about 1.6 mm to about 7 mm.

These curled fibers are further refined using techniques disclosed in U.S. Pat. No. 5,334,176 to Buenger et al., the disclosure of which is hereby incorporated herein by reference. At least about 20% of the resulting fibers, preferably at least about 50%, and more preferably from about 50% to about 90%, and most preferably at least about 90% of the refined fibers have an average length which is from about 10% to about 40% of the length of the original, unrefined curled fibers. Stated in other words, on the average, the unrefined fibers prepared by the process will have lengths in the range from about 1.6 millimeters to about 7 millimeters whereas after refining, the lengths of the refined curled cellulosic fibers will be in the average range from about 0.25 millimeters to about 1.55 millimeters, and have an average of about 0.1 grams to about 0.15 grams of refined fiber per cubic centimeter. The refined wet laid cellulosic fiber may have about 0.05% kymene, by dry weight therein.

Another suitable material that will store the non-fluid portion of body exudates includes a mixture of hydrophilic cellulosic fibers and thermoplastic material which are bonded together into a thermally bonded matrix of the type disclosed in commonly assigned copending U.S. patent application Ser. No. 08/141,156, filed Oct. 21, 1993, in the names of Richards, et al., the disclosure of which is hereby incorporated herein by reference.

Still another suitable material that will store the non-fluid portion of body exudates includes a mixture of hydrophilic cellulosic fibers, thermoplastic material, and eucalyptus fibers which are bonded together in a thermally bonded matrix of the type disclosed in common assigned, copending U.S. patent application, Ser. No. 08/382,817 Case No. 5573 filed Feb. 3, 1995, entitled "Fluid Distribution Member for Absorbent Articles Exhibiting High Suction and High Capacity" in the names of Homey, et al., the disclosure of which is hereby incorporated herein by reference.

The storage component 24 provides an area in and for the storage of fluid portion of the body exudates, and need not have an absorbent capacity much greater than the total amount of exudate to be absorbed. The storage component 24 should have a significant pore volume range from about 5 μm to about 50 μm radii, preferably from about 8 μm to about 30 μm pore radii, to provide sufficient capillary suction for partitioning the fluid portion of the body exudates from acquisition component 22.

Suitable examples of materials useful as storage component 24 include a hydrophilic, flexible structure of interconnected open spaces, such as the hydrophilic foam structure disclosed in U.S. Pat. No. 5,147,345 to Young, the disclosure of which is hereby incorporated herein by reference, or other polymeric foams. Other suitable materials include a superabsorbent polymeric which absorbs fluid to form a hydrogel material, such as the type disclosed in U.S. Pat. No. 5,217,445 to Young, et al., the disclosure of which is hereby incorporated herein by reference. The superabsorbent polymeric material can be dispersed in a fiber matrix (e.g., web or tissue) or can be by in a non-woven sheet. Other known storage components with pore sizes smaller than the range pore sizes in the acquisition component 22, such as airfelt, peat moss, and the like, also can also be used.

In another preferred embodiment, the acquisition component 22 may comprise more than one type of material. FIG. 3 illustrates an alternative embodiment in which the acquisition component 22 comprises a first acquisition component **23*a* and a second fluid acquisition component 23*b*. For optimal absorption efficiency, the first component 23*a* is a separate acquisition-only layer that is interposed between the topsheet 12 and the second component 23*b*, and comprises a material having larger cell sizes and a lower surface area per volume relative to the second component 23b. These structural differences between the materials utilized in first and second component 23a and 23b create a capillary suction between the first and second components 23a and 23b, respectively, and allow for exudates to be more quickly and efficiently absorbed from topsheet 12, fractionated through acquisition component 22, and transported into the storage component 24. Suitable materials useful as materials in acquisition component 23b have a uniformly distributed range of capillary pore volume such as having a radii from about 5 μm to about 150 μm, and preferably from about 5 μm to about 80 μm. Suitable examples of first component 23a** include airfelt, nonwovens, air and wet formed cellulosic webs, and chemically stiffenent cellulose.

Having shown and described the preferred embodiments of the present invention, further adaptions of the absorbent articles of the present invention described herein can be accomplished by appropriate modifications by one of ordinary skill in the art without departing from the scope of the present invention. For example, the absorbent article does not have to be constructed as a laminate and can be constructed as a tubed sanitary napkin or even as a tampon for internal body use whereby the fluid acquisition component of the present invention is wrapped around a suitable storage component. Several such potential modifications have been mentioned, and others will be apparent to those skilled in the art. Accordingly, the scope of the present invention should be considered in terms of the following claims and is understood not to be limited in detail, structure and operation shown and described in its specification and drawings.

We claim:

1. An absorbent structure for the management of a fluid portion and a solid portion of body exudates emanating from a source, said structure comprising:

a) a storage component for storing the fluid portion of the body exudates; and b) an acquisition component interposed between said storage component and the source, said acquisition component comprising a member for fractionating body exudates emanating from the source and for storing the solid portion of the body exudates.

2. The absorbent structure of claim 1, wherein said acquisition component has a pore size average greater than the pore size average of said storage component.

3. The absorbent structure of claim 1, wherein said acquisition component comprises fibers having pore size radii from about 5 μm to about 150 μm.

4. The absorbent structure of claim 3, wherein said acquisition component comprises cellulosic fibers.

5. The absorbent structure of claim 4, wherein said cellulosic fibers comprise chemically stiffened, curled, and twisted cellulosic fibers.

6. The absorbent structure of claim 5, wherein said acquisition component comprises an individualized refined, wet laid curled cellulosic fibers.

7. The absorbent structure of claim 6, wherein said refined fibers comprises at least about 0.05% kymene, by dry weight.

8. The absorbent structure of claim 1, wherein said acquisition component comprises a mixture of cellulosic fibers and thermoplastic material bonded together in a thermally bonded matrix.

9. The absorbent structure of claim 1, wherein said storage component comprises a flexible, hydrophilic polymeric material.

10. The absorbent structure of claim 1, wherein said storage component comprises a superabsorbent polymer which absorbs body exudates to form a swollen hydrogel material.

11. An absorbent article for the management of a fluid portion and solid portion of body exudates, emanating from a source, said article comprising:

a) a backsheet;

b) a storage component interposed between said backsheet and the source, said storage component for storing the fluid portion of the body exudates; and c) an acquisition component interposed between the source and said storage component, said acquisition component comprising a member for fractionating the body exudates emanating from the source and for storing the solid portion of the body exudates.

12. The absorbent structure of claim 11, wherein said acquisition component has a pore size average greater than the pore size average of said storage component.

13. The absorbent structure of claim 11, wherein said acquisition component comprises fibers having pore size radii from about 5 μm to about 150 μm.

14. The absorbent article of claim 13, wherein said acquisition component comprises cellulosic fibers.

15. The absorbent article of claim 14, wherein said cellulose fibers comprise chemically stiffened, twisted, and curled cellulosic fibers.

16. The absorbent article of claim 15, wherein said refined fibers comprise at least about 0.05% kymene, by dry weight.

17. The absorbent article of claim 11, wherein said acquisition component comprises a mixture of hydrophilic cellulosic fibers and thermoplastic material bonding the fibers together in a thermally bonded matrix.

18. The absorbent article of claim 11, wherein said storage component comprises a flexible, hydrophilic polymeric material.

19. The absorbent structure of claim 11, wherein said storage component comprises a superabsorbent polymer, which absorbs body exudates to form a swollen hydrogel material.

20. An absorbent article for the management of a fluid portion and a solid portion of body exudates emanating from a source said article comprising:

a) a backsheet;

b) a storage component interposed between said backsheet and the source, said storage component comprising a hydrophilic flexible polymeric structure of interconnected open cells for storing the fluid portion of body exudates;

c) an acquisition component interposed between the source and said storage component, said acquisition component comprising individualized curled cellulosic fibers that are mechanically altered from an unrefined state to a refined state for fractionating body exudates emanating from the source and for storing the solid portion of the body exudates; and d) a topsheet interposed between the source and said acquisition component.

* * * * *